United States Patent [19]

Bailey

[11] Patent Number: 4,515,980
[45] Date of Patent: May 7, 1985

[54] SUBSTITUTED AMINOBENZOATES, THEIR PREPARATION AND USE

[75] Inventor: Denis M. Bailey, East Greenbush, N.Y.

[73] Assignee: Sterling Drug Inc., New York, N.Y.

[21] Appl. No.: 512,843

[22] Filed: Jul. 11, 1983

[51] Int. Cl.³ .......................................... C07C 101/72
[52] U.S. Cl. ........................................ 560/45; 560/46
[58] Field of Search ...................... 560/45, 46, 47, 48; 424/310, 319

[56] References Cited

U.S. PATENT DOCUMENTS 3,819,637  6/1974  Bell ...................................... 546/165

FOREIGN PATENT DOCUMENTS 13144     7/1980  European Pat. Off. .
50-65528  6/1975  Japan .

OTHER PUBLICATIONS

Molnar et al., Helv. Chim. Acta, 52, 401–408, (1969).
Legrand et al., Bull. Soc. Chim., France, 1969, 1173–82.
Chemical Abstracts, vol. 95, 1981, p. 782, abstract No. 80890q, Kim, D. H., "Synthesis of 5H–benzoxazolo[3,2-a]quinazolin-5-ones".

Primary Examiner—Natalie Trousof
Assistant Examiner—Bruce D. Gray
Attorney, Agent, or Firm—Thomas L. Johnson; B. Woodrow Wyatt; Paul E. Dupont

[57] ABSTRACT

Novel lower-alkyl 2-(hydroxyphenylamino)benzoates, useful as inhibitors of lipoxygenase, are of the formula

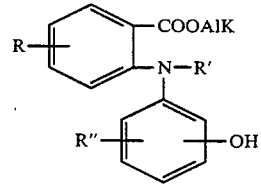

wherein R is hydrogen, lower-alkyl or lower-alkoxy; R' is hydrogen or lower-alkyl; R" is hydrogen, lower-alkyl or halo; and Alk is lower-alkyl. The compounds are prepared by de-etherification of the corresponding alkyl or benzyl ethers.

4 Claims, No Drawings

SUBSTITUTED AMINOBENZOATES, THEIR PREPARATION AND USE

BACKGROUND OF THE INVENTION (1) Field of the Invention

The present invention relates to novel lower-alkyl 2-(hydroxyphenylamino)benzoates, a process for the preparation thereof, and the use of said esters as agents which inhibit lipoxygenase activity.

(2) Information Disclosure Statement

M. R. Bell U.S. Pat. No. 3,819,637, issued June 25, 1974, discloses a chemical formula (XXXIII) as follows:

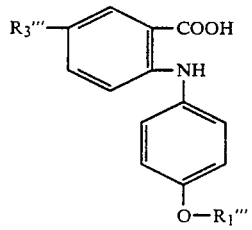

wherein $R_1'''$ is hydrogen, lower-alkyl, benzyl or $C_nH_{2n}NR_4R_5$; and $R_3'''$ is hydrogen, lower-alkyl, lower-alkoxy or halo. Specific compounds disclosed are N-(4-methoxyphenyl)anthranilic acid (Example 14D) and N-(4-benzyloxyphenyl)-5-methoxyanthranilic acid (Example 16C). The compounds are useful as intermediates in preparing tetrahydroquinoline derivatives having antifertility and hypocholesteremic activities.

Molnar et al., Helv. Chim. Acta 52, 401–408 (1969) describe compounds of the formula:

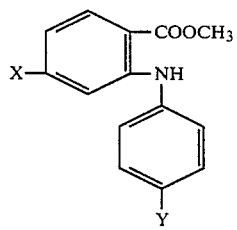

where X is hydrogen, Y is $OCH_2C_6H_5$; X is hydrogen and Y is $OCH_3$; and X is $CH_3O$ and Y is hydrogen. The compounds are intermediates in the preparation of acridane derivatives which are metabolites of the antidepressant drug, dimetacrin.

Legrand et al., Bull. Soc. Chim. France 1969, 1173–82 disclose compounds of the formula

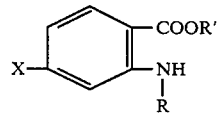

where R is 2- or 4-methoxyphenyl, R' is methyl or ethyl and X is hydrogen or chloro. The compounds are intermediates for the preparation of heterocyclic compounds of undisclosed utility.

Hodogaya Chem. Co. Japanese Disclosure No. 50/65528, published June 3, 1975, discloses 2-(2-methyl-4-hydroxyphenylamino)benzoic acid as a dyestuff intermediate.

ICI European Patent Application No. 13,144, published July 9, 1980, discloses methyl 5-chloro-2-(4-hydroxyphenylamino)benzoate as a herbicide intermediate.

The subject matter of this application is in part disclosed but not claimed in copending Schlegel and Bell U.S. patent application, Ser. No. 485,936, filed Apr. 18, 1983 now U.S. Pat. No. 4,496,590, issued Jan. 29, 1985.

SUMMARY OF THE INVENTION

In a product aspect, the invention relates to compounds of the formula

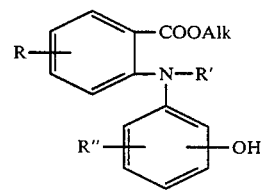

I wherein:

R is hydrogen, lower-alkyl or lower-alkoxy;

R' is hydrogen or lower-alkyl;

R" is hydrogen, lower-alkyl or halo; and

Alk is lower-alkyl.

In a process aspect, the invention relates to a process for preparing a compound of Formula I which comprises (a) de-etherifying a compound of the formula

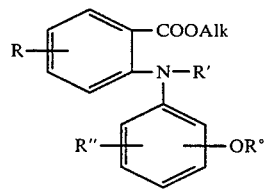

II wherein R° is benzyl or lower-alkyl by a method selected from:

(i) catalytically hydrogenating a compound where R° is benzyl; and (ii) treating a compound where R° is benzyl or lower-alkyl and R is other than lower-alkoxy with a strong protonic acid or a Lewis acid; or (b) esterifying a compound of the formula

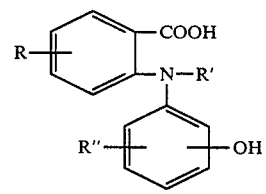

III with a lower-alkanol in the presence of a strong acid.

In a further product aspect, the invention relates to compositions for inhibiting lipoxygenase activity which comprise a compound of the formula

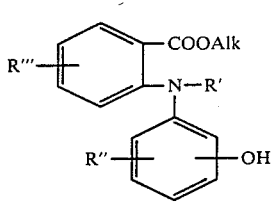

IV wherein:
R' is hydrogen or lower-alkyl;
R" is hydrogen, lower-alkyl or halo;
R'" is hydrogen, lower-alkyl, lower-alkoxy or halo;
and
Alk is lower-alkyl
together with one or more pharmaceutically acceptable excipients or diluents.

In a further process aspect, the invention relates to a method for inhibiting lipoxygenase activity in a mammal which comprises administering to said mammal a composition comprising a pharmacologically effective amount of a compound of Formula IV together with one or more pharmaceutically acceptable excipients or diluents.

DETAILED DESCRIPTION INCLUSIVE OF PREFERRED EMBODIMENTS

In the foregoing Formulas I-IV, the variables R, R', R", R'", R° and Alk when they stand for lower-alkyl or lower-alkoxy include such groups containing from one to three carbon atoms; and when R" or R'" stands for halo, it can be any of the common halogens, fluorine, chlorine, bromine or iodine.

The synthetic approach to the compounds of the invention is outlined in the following flow sheet:

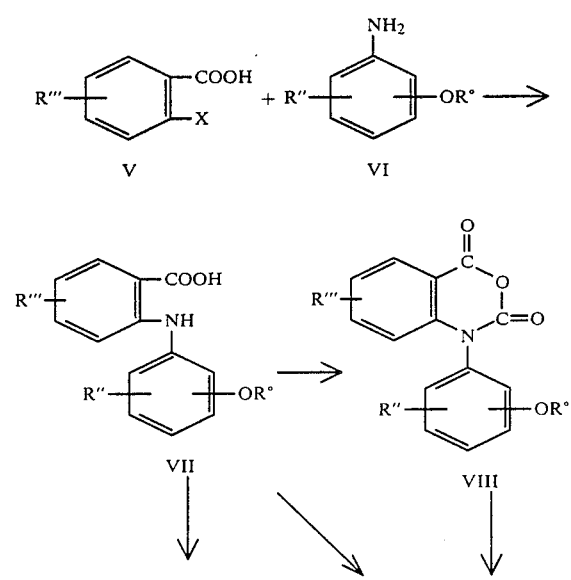

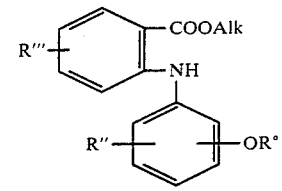

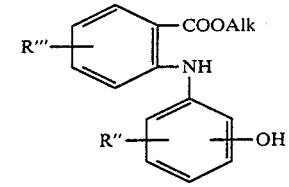

IV (R' = H)

A 2-halobenzoic acid (V, where X is Cl, Br or I) is caused to react with an aminophenol ether (VI), usually in the presence of a catalyst such as cupric acetate, to yield an anthranilic acid derivative of Formula VII. In these formulas, R", R'" and R° have the meanings given hereinabove.

An acid of Formula VII can be esterified to form an ester of Formula X by conventional means, as by reacting the acid with a lower-alkanol in the presence of a strong acid; or by reacting the acid with a di-lower-alkyl sulfate in the presence of a strong base. Esterification can also be effected by converting the acid to the corresponding isatoic acid anhydride VIII and reacting the latter with di-alkylzinc. The intermediate of Formula VIII is formed from the acid (VII) by reaction with phosgene.

An ester of Formula X can be converted to a phenolic ester of Formula IV by dealkylation (R° = lower-alkyl) with a protonic or Lewis acid, or debenzylation (R° = benzyl) by catalytic hydrogenation or acid treatment. A preferred reagent for dealkylation is boron tribromide.

An alternate route to a compound of Formula IV is by de-etherification of an acid of Formula VII to a phenolic acid of Formula IX and esterification of the latter with a lower-alkanol in the presence of a strong acid, heated at a temperature between about 50° and 120° C.

If a compound of Formula I or IV where R' is lower-alkyl is desired, it can be obtained by N-alkylation of an intermediate of Formula X, followed by de-etherification. The N-alkylation is effected with a lower-alkyl halide (preferably bromide or iodide) in the presence of a strong base.

EXAMPLE 1

(a) 2-(2-Methoxyphenylamino)benzoic acid [VII; R"=H, OR°=2-OCH$_3$, R'"=H]

A mixture of 40 g (0.25 mole) of 2-chlorobenzoic acid, 21 ml (0.26 mole) of 2-methoxyaniline, 3.84 g cupric acetate, 35.4 g of potassium carbonate and 155 ml of dimethylformamide was heated at 120° C. for 12 hours. The reaction mixture was poured into ice-water, acidified with concentrated hydrochloric acid to pH 2, and stirred for one hour. The solid product was collected by filtration, air dried and recrystallized from toluene to give 28.61 g of 2-(2-methoxyphenylamino)-benzoic acid.

(b) N-(2-Methoxyphenyl)isatoic anhydride [VIII; R″=H, OR°=2-OCH$_3$, R‴=H]

To a suspension of 24.44 g (0.177 mole) of potassium carbonate in 119 ml of toluene and 238 ml of water, stirred at 20°–40° C., was added 28.61 g (0.1176 mole) of 2-(2-methoxyphenylamino)benzoic acid, and phosgene was bubbled through the mixture for a period of 3.5 hours. The reaction was allowed to stand overnight with stirring, and the solid material was collected by filtration. The latter was dissolved in ethyl acetate and added to the toluene layer separated from the filtrate. The solution was washed twice with 200 ml 1N potassium hydroxide and dried over anhydrous magnesium sulfate. The solvent was removed in vacuo to yield 7 g of N-(2-methoxyphenyl)isatoic anhydride.

(c) Ethyl 2-(2-methoxyphenylamino)benzoate [X; R″ and R‴=H, OR°=2-OCH$_3$, Alk=C$_2$H$_5$]

N-(2-Methoxyphenyl)isatoic anhydride (1 g, 0.00369 mole), 4 ml (0.00532 mole) of 1.33M diethylzinc in 4 ml of tetrahydrofuran, and 15 ml of tetrahydrofuran were combined at 0°–5° C. and then stirred at room temperature for two days. The reaction mixture was poured into water and extracted with ether. The ether extracts were washed with 20 ml of 1N potassium hydroxide, then dried over anhydrous magnesium sulfate and concentrated. The residue (1.12 g) was flash chromatographed on silica gel using 5% ethyl acetate/95% hexane as eluant to afford ethyl 2-(2-methoxyphenylamino)benzoate as a yellow viscous liquid, b.p. 284°–286° C. (760 mm).

(d) Ethyl 2-(2-hydroxyphenylamino)benzoate [I; R, R′ and R″=H, Alk=C$_2$H$_5$, OH at 2-position]

A solution of 9.74 g (0.0359 mole) of ethyl 2-(2-methoxyphenylamino)benzoate in 50 ml of methylene dichloride was cooled to −78° C. and 114 ml of boron tribromide (1M in methylene dichloride) was added dropwise over a period of 20 minutes. The reaction mixture was stirred at −78° C. for three hours, then at −40° C. for one hour and finally kept in a refrigerator at −4° C. overnight. Ether (50 ml) was added and the mixture poured into ice-water and ether. The ether solution was separated, dried over anhydrous magnesium sulfate and concentrated. The residue was recrystallized from acetonitrile to give 5.3 g of ethyl 2-(2-hydroxyphenylamino)benzoate, m.p. 105°–106° C.

EXAMPLE 2

(a) Ethyl 2-(4-methoxyphenylamino)benzoate [X; R″ and R‴=H, OR°=4-OCH$_3$, Alk=C$_2$H$_5$] was prepared from N-(4-methoxyphenyl)isatoic anhydride and diethylzinc according to the procedure of Example 1, part (c) and was obtained in 88% yield as a yellow powder, m.p. 76°–77° C. when recrystallized from ethanol.

The starting material, N-(4-methoxyphenyl)isatoic anhydride was prepared from 2-(4-methoxyphenylamino)benzoic acid and phosgene according to the procedure of Example 1, part (b).

(b) Ethyl 2-(4-hydroxyphenylamino)benzoate [I; R, R′ and R″=H, Alk=C$_2$H$_5$, OH at 4-position] was prepared by reaction of ethyl 2-(4-methoxyphenylamino)-benzoate with boron tribromide according to the procedure of Example 1, part (d), and was obtained in 38% yield as a yellow solid, m.p. 103°–104° C. when recrystallized from aqueous ethanol.

The corresponding free acid, 2-(4-hydroxyphenylamino)benzoic acid, yellow solid m.p. 233° C.(decompn.) was prepared by hydrogenation of 5 g of 2-(4-benzyloxyphenylamino)benzoic acid in 250 ml of ethanol containing 2 ml of concentrated hydrochloric acid and 2 g of palladium-on-carbon catalyst. The benzyloxy compound was in turn prepared by reaction of 2-chlorobenzoic acid and 4-benzyloxyaniline.

EXAMPLE 3

(a) 2-(4-Benzyloxyphenylamino)-5-methoxybenzoic acid

To a 5 L 3-neck flask was added 284 g (2.06 moles) milled potassium carbonate and 1.0 L dimethylformamide. While stirring the resulting mixture at room temperature, 250 g (1.06 moles) 4-benzyloxyaniline hydrochloride was added portionwise over 15 minutes. After this was completed, 231 g (1.0 mole) 2-bromo-5-methoxybenzoic acid was added over 15 minutes and the mixture was stirred for another 15 minutes. The suspension was cooled to 10°–15° C. and 13.8 g cupric acetate monohydrate (0.06 moles) was added portionwise over 20 minutes. Gas evolved slowly and after stirring 15 minutes at room temperature the reaction was warmed on a steam bath over 40 minutes to 70° C. whereupon a vigorous evolution of carbon dioxide was observed. Stirring and heating was continued for 90 minutes at 80°–85°C., heat was removed and the mixture was allowed to cool to room temperature. The brownish red suspension was transferred to a 12 L flask containing 1 L ice-cold water. Acetic acid (650 ml) was added dropwise and the dark green precipitate was stirred vigorously until homogeneous. After filtering and washing well with water, the crude product was dried overnight at 55°–60° C. in a vacuum oven. The crude product (approximately 350 g) was diluted with 5.8 L toluene, heated to reflux temperature and filtered. The dark green filtrate was allowed to cool to room temperature for 2–3 hours, and the solid product was collected by filtration and rinsed with cold (5°–10° C.) toluene. The bright yellow crystalline product was obtained in 80% yield. A sample of the compound had the m.p. 167°–168° C. when recrystallized from a benzene-cyclohexane mixture.

(b) N-(4-Benzyloxyphenyl)-5-methoxyisatoic anhydride

[VIII; R″=H, OR°=4-OCH$_2$C$_6$H$_5$, R‴=5-CH$_3$O] was prepared from 2-(4-benzyloxyphenylamino)-5-methoxybenzoic acid and phosgene according to the procedure of Example 1, part (b), and was obtained in 79% yield as a colorless solid used directly in the next reaction.

(c) Ethyl 2-(4-benzyloxyphenylamino)-5-methoxybenzoate [X; R″=H, OR°=4-OCH$_2$C$_6$H$_5$, R‴=5-CH$_3$O, Alk=C$_2$H$_5$] was prepared from N-(4-benzyloxyphenyl)-5-methoxyisatoic anhydride and diethylzinc according to the procedure of Example 1, part (c), and was obtained in about 90% yield as a yellow solid, m.p. 61°–62° C. when recrystallized from isopropyl alcohol.

(d) Ethyl 2-(4-hydroxyphenylamino)-5-methoxybenzoate [I; R=5-CH$_3$O, R′ and R″=H, Alk=C$_2$H$_5$, OH at 4-position]

A mixture of 6 g of ethyl 2-(4-benzyloxyphenylamino)-5-methoxybenzoate, 30 ml of acetic acid, 270 ml of ethanol and 500 mg of 10% palladium-on-carbon catalyst was hydrogenated on a Parr apparatus for eight hours. The mixture was filtered, the filtrate stripped of solvent and the residue partitioned between ether and saturated sodium bicarbonate solution. The ether solution was dried over anhydrous magnesium sulfate and the solvent removed to give 5.6 g of ethyl 2-(4-hydroxyphenylamino)-5-methoxybenzoate as a yellow solid, m.p. 134°-136° C. when recrystallized from toluene.

The corrresponding free acid, 2-(4-hydroxyphenylamino)-5-methoxybenzoic acid, golden solid, m.p. 186°-187° C., was prepared by hydrogenation of 2-(4-benzyloxyphenylamino)-5-methoxybenzoic acid [cf. part (a) above].

EXAMPLE 4

(a) 2-(4-Methoxy-2-methylphenylamino)benzoic acid [VII; R''=2-CH$_3$, OR°=4-OCH$_3$, R'''=H] was prepared from 2-chlorobenzoic acid and 4-methoxy-2-methylaniline according to the procedure of Example 1, part (a), and was obtained in 59% yield as a grey solid used directly in the next reaction.

(b) Ethyl 2-(4-methoxy-2-methylphenylamino)benzoate [X; R''=2-CH$_3$, OR°=4-OCH$_3$, R'''=H, Alk=C$_2$H$_5$]

Dimethylformamide (250 ml) was added to sodium hydride (obtained from 4.80 g of 50% oil dispersion after washing and drying) and the mixture cooled to 0°-5° C. 2-(4-Methoxy-2-methylphenylamino)benzoic acid (25.7 g) was then added, and the mixture was stirred at room temperature for 45 minutes and then cooled to 0°-5° C. To the latter mixture was added 13 ml of diethyl sulfate, and the reaction mixture was stirred overnight at room temperature and poured into a mixture of ether, acetic acid, water and ice. The mixture was extracted with ether and the ether extracts washed with 1N potassium hydroxide and dried over anhydrous magnesium sulfate. Removal of the ether and crystallization of the residue from isopropyl alcohol gave 12.2 g of ethyl 2-(4-methoxy-2-methylphenylamino)benzoate as a pale yellow solid, m.p. 42°-43° C.

(c) Ethyl 2-(4-hydroxy-2-methylphenylamino)benzoate [I; R and R'=H, R''=2-CH$_3$, Alk=C$_2$H$_5$, OH at 4-position] was prepared by reaction of ethyl 2-(4-methoxy-2-methylphenylamino)benzoate with boron tribromide according to the procedure of Example 1, part (d), and was obtained in the form of a yellow solid, m.p. 103°-105° C. when recrystallized from cyclohexane.

The corresponding free acid, 2-(4-hydroxy-2-methylphenylamino)benzoic, obtained as byproduct, had the m.p. 209°-211° C. (decompn.).

EXAMPLE 5

(a) 2-(3-Chloro-4-methoxyphenylamino)benzoic acid [VII; R''=3-Cl, OR°=4-OCH$_3$, R'''=H] was prepared from 2-chlorobenzoic acid and 3-chloro-4-methoxyaniline according to the procedure of Example 1, part (a), and was obtained in 68% yield as a solid recrystallized from acetonitrile and used directly in the next reaction.

(b) Ethyl 2-(3-chloro-4-methoxyphenylamino)benzoate [X; R''=3-Cl, OR°=4-OCH$_3$, R'''=H, Alk=C$_2$H$_5$] was prepared by esterification of 2-(3-chloro-4-methoxyphenylamino)benzoic acid with diethyl sulfate in the presence of sodium hydride according to the procedure of Example 4, part (b), and was obtained in 48% yield as a pale yellow solid, m.p. 118.5°-119.5° C. when recrystallized from acetonitrile.

(c) Ethyl 2-(3-chloro-4-hydroxyphenylamino)benzoate [I; R and R'=H, R''=3-Cl, Alk=C$_2$H$_5$, OH at 4-position] was prepared by reaction of ethyl 2-(3-chloro-4-methoxyphenylamino)benzoate with boron tribromide according to the procedure of Example 1, part (d), and was obtained in about 50% yield as a pale yellow solid, m.p. 87°-88° C. when recrystallized from cyclohexane.

The corresponding free acid, 2-(3-chloro-4-hydroxyphenylamino)benzoic acid, obtained by treating its methyl ether with boron tribromide, had the m.p. 180°-183° C., yellow solid from acetonitrile.

EXAMPLE 6

(a) 4-Chloro-2-(4-methoxyphenylamino)benzoic acid [VII; R''=H, OR°=4-OCH$_3$, R'''=4-Cl] was prepared from 2,4-dichlorobenzoic acid and 4-methoxyaniline according to the procedure of Example 1, part (a), and was obtained in about 60% yield as a green-gray solid.

(b) 4-Chloro-2-(4-hydroxyphenylamino)benzoic acid [IX; R''=H, R'''=4-Cl, OH at 4-position] was prepared by treating 4-chloro-2-(4-methoxyphenylamino)benzoic acid with boron tribromide according to the procedure of Example 1, part (d), and was obtained as a tan solid, m.p. 217° C. (decompn.) when recrystallized from aqueous ethanol.

(c) Methyl 4-chloro-2-(4-hydroxyphenylamino)benzoic acid
[I; R=4-Cl, R' and R''=H, Alk=CH$_3$, OH at 4-position] is obtainable by esterification of 4-chloro-2-(4-hydroxyphenylamino)benzoic acid with methanol and hydrochloric acid; or by esterification of 4-chloro-2-(4-methoxyphenylamino)benzoic acid with dimethyl sulfate, followed by de-etherification of the resulting methyl 4-chloro-2-(4-methoxyphenylamino)benzoate with boron tribromide.

EXAMPLE 7

(a) 5-Chloro-2-(4-benzyloxyphenylamino)benzoic acid [VII; R''=H, OR°=4-OCH$_2$C$_6$H$_5$, R'''=5-Cl] was prepared from 2,5-dichlorobenzoic acid and 4-benzyloxyaniline according to the procedure of Example 1, part (a), and was obtained as a yellowish-green solid, m.p. 189°-191° C.

(b) Ethyl 5-chloro-2-(4-hydroxyphenylamino)benzoate [I; R=Cl, R' and R''=H, Alk=C$_2$H$_5$, OH at 4-position] is obtainable by esterification of 5-chloro-2-(4-benzyloxyphenylamino)benzoic acid with diethyl sulfate, followed by de-etherification by catalytic hydrogenation or by heating with a strong acid.

EXAMPLE 8

(a) Methyl 2-[methyl-(4-benzyloxyphenyl)amino]benzoate [II; R=H, R'=CH$_3$, R''=H, OR°=4-OCH$_2$C$_6$H$_5$, Alk=CH$_3$]

2-(4-Benzyloxyphenylamino)benzoic acid (30.0 g, 0.094 mole) was added portionwise to a stirred suspension of sodium hydride (0.376 mole, from 18.0 g of 50% oil suspension washed with pentane) in 300 ml of dimethylformamide cooled in an ice-bath. The ice-bath was removed and the reaction mixture stirred for 35 minutes. The ice-bath was then replaced and 23.4 ml of methyl iodide added dropwise over 12 minutes. After stirring the mixture for one hour at room temperature, it was again cooled and an additional 12 ml of methyl iodide added. The reaction mixture was stirred for about 16 hours, then poured into ice-water and extracted with ethyl acetate. The extract was dried over magnesium sulfate and concentrated to an oil which crystallized (35.8 g). The latter, comprising a mixture of methyl 2-(4-benzyloxyphenylamino)benzoate and its N-methyl derivative, was chromatographed on silica and the major factions recrystallized from isopropyl alcohol to give said N-methyl derivative, 25.3 g, m.p. 57°–59° C.

(b) Methyl 2-[methyl-(4-hydroxyphenyl)amino]benzoate [I; R=H, R'=CH$_3$, R"=H, Alk=CH$_3$, OH at 4-position] is obtainable by de-etherification of methyl 2-[methyl-(4-benzyloxyphenyl)amino]benzoate by catalytic hydrogenation.

The compounds of Formulas I and IV have been found to inhibit lipoxygenase activity in biological systems, thus indicating their usefulness as anti-asthmatic agents.

Slow reacting substance of anaphylaxis (SRS-A) is a descriptive term for a family of lipoxygenase metabolic products of arachidonic acid designated as the leukotrienes. These substances are potent contractile agents of vascular and pulmonary smooth muscle. The relationship of SRS-A to asthma was first characterized by Brockelhurst [Rev. in Adv. Drug Res. 19, 109 (1970)] who identified the material as being present subsequent to specific antigen challenge of living tissue obtained from asthmatic patients. Herxheimer and Stressmann [J. Physiol. 165, 78P (1953)] first demonstrated that aerosolized guinea pig SRS-A induced bronchospasm in man. This observation has been more recently confirmed using purified leukotrienes.

Recent studies have indicated that lipoxygenase inhibiting compounds may have therapeutic potential in treating diseased states other than asthma, e.g. bronchitis, acute inflammation, arthritis, psoriasis, cardiovascular insufficiency and myocardial infarct.

The primary screening test used is a determination of the inhibition of lipoxygenase and cyclooxygenase derived from rat basophilic leukemia (RBL-1) cells. The test was carried out according to the following procedure:

Single cell suspensions of RBL-1 cells are homogenized to obtain the microsomal fraction containing lipoxygenase and cyclooxygenase. Test compounds are added to the enzyme-containing homogenate for a 5 min preincubation period at 37° C. prior to the addition of $^{14}$C-arachidonic acid substrate. Following incubation at 37° C. for 15 min, the reaction is stopped by the addition of 2M formic acid and the enzyme-substrate products are extracted into chloroform. An aliquot of the extract is evaporated to dryness, reconstituted in ether to 1/10 original volume, spotted on thin layer chromatography plates and chromatographed. The peak areas of radioactivity representing the products are located by scanning the plates. The quantity of products formed is estimated by measuring the height of the radioactivity peaks observed on the chromatographic scans. Alternatively, the areas of radioactivity are scraped from the plate and the $^{14}$C quantitated by scintillation counting. The percent inhibition in the formation of the cyclooxygenase product PDG2, designated as C1 and lipoxygenase products, L1 designated for 5,12-di-HETE and L2 for 5-HETE are shown. Compounds with >50% inhibition of L1 and L2 at a screening concentration of 1 μm are considered active.

The in vivo activity was measured by the effect on the STS-A component of immunologically induced bronchoconstriction in guinea pigs. The test was carried out according to the following procedure:

Two weeks after immunization with egg albumin, guinea pigs are prepared for bronchoconstriction determination. One hour prior to antigen challenge, each animal is dosed orally with indomethacin and chlorpheniramine. Animals are anesthetized with sodium pentobarbital, the trachea cannulated and the animal artifically respired. Arachidonic acid is administered intravenously prior to antigen challenge. The resulting bronchoconstriction is recorded by the standard lung overflow procedure and the peak increase in intratracheal pressure (mm Hg) over a 10 minute observation period is recorded. Compounds are evaluated for their ability to prevent the increased intratracheal pressure in an experimental group of animals as compared to the medicated (indomethacin+chlorpheniramine+arachidonic acid) control group. The results are expressed in terms of percent inhibition or as ED$_{50}$ values (efffective dose in 50% of the animals).

The following Table summarizes the results obtained from the testing of specific compounds of the invention.

| Example No. | | In vitro | | In vivo Guinea Pig |
|---|---|---|---|---|
| | | % Inhibition[a] | IC$_{50}$[b] | |
| 1d | C1 | 34 | 0.32 | |
| | L1 | 95 | 0.16 | |
| | L2 | 98 | 0.10 | |
| 2b | C1 | 19 | >1 | 38% inhib. (4 hrs.) |
| | L1 | 77 | 0.34 | at 1 mg/kg orally |
| | L2 | 93 | 0.25 | |
| 3d | C1 | 18 | >1 | 42% inhib. (4 hrs.) |
| | L1 | 90 | 0.11 | at 1 mg/kg orally |
| | L2 | 91 | 0.10 | |
| 4c | C1 | 0 | | |
| | L1 | 60 | | |
| | L2 | 76 | | |
| 5c | C1 | 26 | >1 | |
| | L1 | 90 | 0.67 | |
| | L2 | 99 | 0.30 | |

[a]Percent inhibition of cyclooxygenase (C1) and lipoxygenase (L1 and L2) formation at a dose of 1 μM.
[b]Inhibitory concentration (μM) in 50% of tests.

The compounds of the invention can be prepared for use by conventional pharmaceutical procedures: that is, by dissolving or suspending them in a pharmaceutically acceptable vehicle, e.g., water, aqueous alcohol, glycol, oil solution or oil-water emulsion, for parenteral or oral administration; or by incorporating them in unit dosage form as capsules or tablets for oral administration either alone or in combination with conventional adjuvants or excipients, e.g., calcium carbonate, starch, lactose, talc, magnesium stearate, gum acacia, and the like.

I claim:

1. A compound of the formula

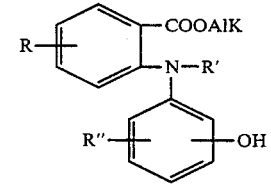

wherein:
 R is lower-alkoxy;
 R' is hydrogen or lower-alkyl;
 R" is hydrogen, lower-alkyl or halo; and
 Alk is lower-alkyl.

2. A compound according to claim 1 wherein R' is hydrogen.

3. Ethyl 2-(4-hydroxyphenylamino)-5-methoxybenzoate, according to claim 2.

4. Ethyl 2-(4-hydroxyphenylamino)benzoate.

* * * * *

UNITED STATES PATENT AND TRADEMARK OFFICE
CERTIFICATE OF CORRECTION

PATENT NO. : 4,515,980
DATED : May 7, 1985
INVENTOR(S) : Denis M. Bailey

It is certified that error appears in the above-identified patent and that said Letters Patent is hereby corrected as shown below:

Column 9, line 60, "μm" should read --μM--; and line 62, "STS-A" should read --SRS-A--.

Signed and Sealed this

Seventh Day of January 1986

[SEAL]

Attest:

DONALD J. QUIGG

Attesting Officer

Commissioner of Patents and Trademarks